Figure 1:
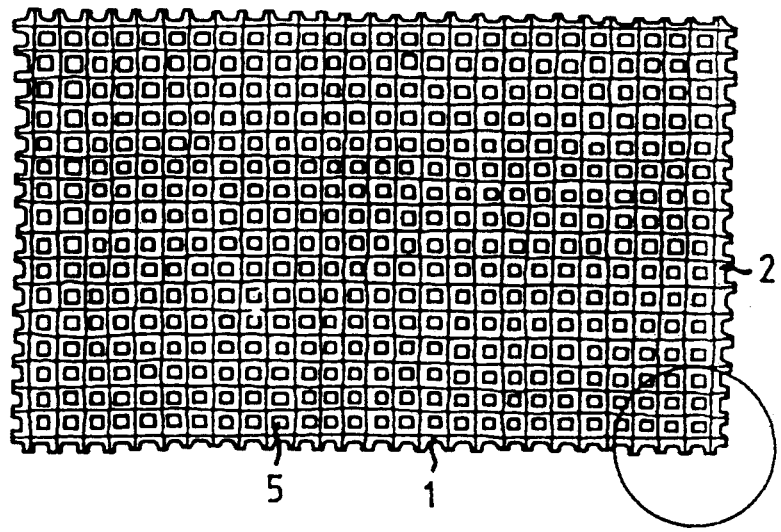

United States Patent

Fabo

[11] Patent Number: 5,340,363
[45] Date of Patent: Aug. 23, 1994

[54] WOUND DRESSING

[75] Inventor: Tomas Fabo, Mölnlycke, Sweden

[73] Assignee: Molnlycke AB, Goteborg, Sweden

[21] Appl. No.: 491,936

[22] Filed: Mar. 12, 1990

Related U.S. Application Data

[60] Division of Ser. No. 313,363, Feb. 19, 1989, Pat. No. 4,921,704, which is a continuation of Ser. No. 126,141, Nov. 3, 1987, abandoned.

[30] Foreign Application Priority Data

Mar. 10, 1986 [SE] Sweden ................ 8601098

[51] Int. Cl.5 ............... A61F 13/00; A61F 15/00; A61L 15/00
[52] U.S. Cl. ........................... 604/304; 602/48; 424/446; 424/447
[58] Field of Search ........... 128/156; 424/443, 445, 424/446, 447; 604/304; 602/48, 47

[56] References Cited

U.S. PATENT DOCUMENTS

| 4,307,717 | 12/1981 | Hymes et al. | 128/156 |
| 4,608,044 | 8/1986 | Nordqvist et al. | 128/156 |
| 4,838,253 | 6/1989 | Brassington et al. | 128/156 |
| 4,921,704 | 5/1990 | Fabo | 128/156 |

OTHER PUBLICATIONS

Hawley's Condensed Chemical Dictionary, 11th Ed, (1987), p. 1162.

Primary Examiner—Randall L. Green
Assistant Examiner—Paul Prebilic
Attorney, Agent, or Firm—Young & Thompson

[57] ABSTRACT

A wound dressing for use with exuding wounds is provided comprising a porous hydrophobic layer adapted to directly contact the wound during use and an adjacent absorbent layer attached to said hydrophobic layer, said hydrophobic layer comprised of an elastic net-like porous reinforcing component substantially completely encapsulated by a soft and elastic hydrophobic gel while retaining the porosity of said reinforcing component, said hydrophobic layer thus including openings which permit wound exudate to pass through said hydrophobic layer to be absorbed by said outer absorbent layer.

6 Claims, 1 Drawing Sheet

WOUND DRESSING

This application is a division of application Ser. No. 07/313,363 filed Feb. 21, 1989, U.S. Pat. No. 4,921,704 which is a continuation of application Ser. No. 07/126,141, filed Nov. 3, 1987, now abandoned.

A wound healing process may principally be subdivided into three phases. The wound is first cleaned out followed by the formation of new tissue, whereafter the restored tissues during a final maturing phase stabilize while developing a less brittle and more elastic structure.

The regeneration phase involves the growth of capillaries, fibroblasts and epithelium into the wound site for building up new tissue. The newly formed tissue is extremely delicate and supersensitive to external influences. If a wound still in progress of regenerating tissue is covered with a dressing composed of a fibrous material, the fibers may easily intermingle with the newly formed tissues and give rise to inflammatory reactions in the wound tissue, which would result in deterioration of the wound healing process. Furthermore, the wound tissue would also be mechanically damaged in connection with removal and change of dressing. To avoid this, it is extremely important for the dressing applied to the wound not to get stuck in dried-up wound exudate, or in any coagulum possibly formed. To attain the most favorable conditions for optimal wound healing, the wound should be kept moist but free of excess wound exudate during this phase of wound repair.

Wound dressings intended for use during this particularly sensitive stage of the wound healing process should therefore be designed so as not to stick to the wound bed; they should be pliable and have a soft wound-contacting surface. In addition, the dressings must be capable of seeping up excess amounts of wound fluid, or to allow for the passage of fluid exudate into an absorbent body placed over the dressing.

Commonly used types of dressings for application to wounds in the regenerating phase are pads soaked with ointment and made of gauze or nylon netting, possibly in combination with an absorbent body. Dressings of this type, as compared with conventional fibrous dressings, have a low tendency of sticking to the wound due to their poor adhesivity towards wound tissue. However, there are associated with the use of such dressings numerous drawbacks and disadvantages. For example, ointment easily falls off during use of this dressing admitting thereby a foreign substance to enter the wound, which would negatively affect the wound healing process. The pads soaked with ointment are smeary and unpleasant to handle and, although impregnated, they often stick tenaciously to the wound bed thus giving rise to tissue damages.

Another type of dressing used on wounds in the regenerating stage constitutes a combination of a perforated polymer or metal film and a more or less absorbent body made of a fibrous material. The idea is for the film to produce a non-frictional, hydrophobic wound-contacting surface preventing in this manner the dressing from sticking to the wound. Dressings of this type are stiff, inelastic and non-flexible. The greatest disadvantage with such prior art dressings, however, is the fact that despite their smooth surface, they still get stuck in the wound bed much too often.

With the present invention there has been achieved a wound dressing which does not stick to healing wound tissue and which substantially does not give off fibers or other components harmfully affecting the wound healing process.

A wound dressing according to the invention is primarily distinguished in that it comprises a soft and elastic hydrophobic gel lying in direct contact with the wound bed during use of the dressing and being built up on a reinforcement netting made of an elastic material, said gel being applied to seal around all constituents of the netting while leaving through-holes in the layer composed of gel and reinforcement.

To accomplish a wound dressing having properties such as low tendency of sticking to wound tissue and poor solubility in aqueous media such as wound fluid for example, the gel incorporated in the dressing must necessarily be hydrophobic.

According to a particularly advantageous embodiment of the invention, the hydrophobic gel is a silicone gel.

Figure 2:
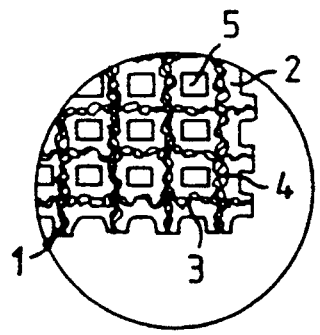

The invention will be described in more detail below with reference to an exemplary embodiment illustrated in the accompanying drawing, of which FIG. 1 is a plan view of a wound dressing according to the invention, and FIG. 2 is a partially enlarged view of the dressing as shown in FIG. 1.

The dressing shown in FIGS. 1 and 2 comprises a reinforcement 1 in the form of an elastic, hydrophobic, knitted network and a silicone gel layer 2 applied to seal around the threads of the reinforcement 1 which is thereby encapsulated by the gel. In order for the dressing to perform its optimal function, the encapsulation must be almost complete with only a strictly limited number of fiber ends being allowed to penetrate the silicone gel and project out of the dressing surface.

The gel must be securely fixed to the reinforcement 1 for maintaining the gel layer 2 substantially intact during use of the dressing, avoiding in this manner any disturbance of the wound healing process such as inflammatory reactions caused by loose gel fragments.

When, as in the example shown in FIG. 1, the gel seals around the structural elements included in the reinforcement 1 constituting here the individual threads 3 of the netting, it will form a continuous, three-dimensionally extended layer which is in itself strong enough to keep the reinforcement well encapsulated.

In order to provide a higher degree of security against disintegration of the gel layer, the reinforcing threads 3 may, as shown in FIG. 2, be composed of a plurality of loosely twisted fibers 4. With such an arrangement the silicone gel will penetrate between each individual fiber in the threads of the netting, adding in this manner to the strength of the gel layer.

Thus, the gel does not necessarily have to adhere to the reinforcement material for the dressing to present a continuous and stable outer layer of gel.

The openings 5 in the net allows for the passage of excess wound exudate through the dressing. For the treatment of wounds under regeneration of skin tissue, a dressing according to the invention is preferably combined with an absorbent bandage applied over the gel-coated netting. In this manner excessive amounts of wound exudate will be sucked up at the same time as the absorbent bandage is kept spaced from the wound bed thereby preventing the bandage from sticking to the wound. If necessary, the distance between the absorbent bandage and the wound tissue can be further increased by superimposing several layers of gel-coated netting on the wound surface before applying the absorbent bandage.

Owing to its flexibility and its capability of adhering to dry skin, the silicone gel netting can be easily affixed over the wound site. The strongly hydrophobic nature of the silicone gel prevents wound fluid from penetrating out over the healthy skin surrounding the wound and to loosen up skin tissue. The net-like structure of the dressing allows for the surrounding, healthy area of the skin to which the dressing is affixed to be maintained airy and rich in oxygen.

The net coated with silicone is easily re-shapable and self-adhering, allowing thereby several layers of the net to be applied in a superimposed position. Due to its pliability, the dressing can further be used for filling in deep wound cavities enabling thereby the wound edges to be kept apart during the wound healing process. In this manner the wound is prevented from closing together by contraction of the wound edges while also reducing the risk of disfiguring and motion-inhibiting scars due to the gradual formation of new tissue from the wound edges, the wound cavity successively being filled in with regenerated tissue.

As an example of a silicone gel having the properties required for this purpose can be mentioned a type of-gel marketed by Dow Corning under the registered tradename Dow Corning Q7-2218-Silicone Gel System, which is a two-component system that produces a cross-linked, tacky silicone gel.

The hydrophobic character of the silicone gel makes it particularly useful as a carrier for medicaments soluble in fat such as pain-relieving substances. for example. It is also conceivable to have antibacterial agents, or agents stimulating wound repair, incorporated in the gel. An example of the lastmentioned type of agent is zinc.

The exemplary embodiment described in the foregoing is merely intended to illustrate the inventive concept without restricting its scope.

The silicone gel described in the example could naturally be replaced by any other hydrophobic gel having similar properties in other respects. For example, polyurethane gel could be used as an alternative to silicone gel.

Many modifications of the invention are conceivable within the scope of the patent claims.

In a suitable embodiment the reinforcement could be made of a polyurethane foam being immersed in a bath of silicone gel to accomplish the wound dressing.

What is claimed is:

1. A liquid permeable wound dressing which is non-adherent to wounds comprising one or more sheets of apertured liquid permeable material coated with a sufficient amount of cross-linked tacky silicone gel to effectively encapsulate the one or more sheets of apertured liquid permeable material but insufficient to occlude the apertures therein.

2. The dressing according to claim 1, wherein the apertured liquid permeable material is a soft, flexible and elastically extendable net of textile material.

3. The dressing according to claim 1, wherein the apertured liquid permeable material is a netting having a knitted, crocheted or woven performance.

4. The wound dressing according to claim 1, further comprising a fat-soluble medicament carried by said silicone gel.

5. The dressing according to claim 1, further comprising an anti-bacterial agent incorporated in said silicone gel.

6. The dressing according to claim 5, wherein said anti-bacterial agent is zinc.

* * * * *